United States Patent [19]
Sellers

[11] Patent Number: 4,986,753
[45] Date of Patent: * Jan. 22, 1991

[54] DIRECT ASSEMBLY FRAMEWORK FOR AN OSSEOINTEGRATED IMPLANT

[76] Inventor: Grady C. Sellers, Rte. 3, Box 79, Sulphur Springs, Tex. 75482

[*] Notice: The portion of the term of this patent subsequent to Apr. 10, 2007 has been disclaimed.

[21] Appl. No.: 506,693

[22] Filed: Apr. 9, 1990

Related U.S. Application Data

[63] Continuation-in-part of Ser. No. 181,919, Apr. 15, 1988, Pat. No. 4,915,629.

[51] Int. Cl.$^5$ ............................................. A61C 13/12
[52] U.S. Cl. ..................................... 433/172; 433/173
[58] Field of Search .............. 433/172, 173, 174, 175, 433/176, 167, 169

[56] References Cited

U.S. PATENT DOCUMENTS

| | | | |
|---|---|---|---|
| 973,343 | 10/1910 | Corcoran | 433/172 |
| 3,955,280 | 5/1976 | Sneer | 433/173 |
| 4,086,701 | 5/1978 | Kawahara et al. | 433/174 |
| 4,547,156 | 10/1985 | Hader | 433/172 |

FOREIGN PATENT DOCUMENTS

| | | | |
|---|---|---|---|
| 3413811 | 4/1984 | Fed. Rep. of Germany | 433/169 |
| 655437 | 4/1985 | Switzerland | 433/173 |

Primary Examiner—John J. Wilson
Attorney, Agent, or Firm—David H. Judson

[57] ABSTRACT

The present invention relates to a framework for a fixed/detachable prosthesis that is assembled intraorally onto at least one abutment supported by an osseointegrated implant. The framework comprises a cast member having an upper surface for supporting an aesthetic veneer and a lower surface having a recess therein, the cast member having a fastener support located above the recess and comprising a flange and a retaining wall projecting out from an upper edge of the flange. A sleeve is supported on the abutment between the abutment and the recess in the lower surface, and a preferably flathead fastener is supported in the retaining wall for securing the cast member to the abutment. A cement composition is provided in the recess in the lower surface to insure accurate adaptation of the cast member to the abutment upon installation.

11 Claims, 5 Drawing Sheets

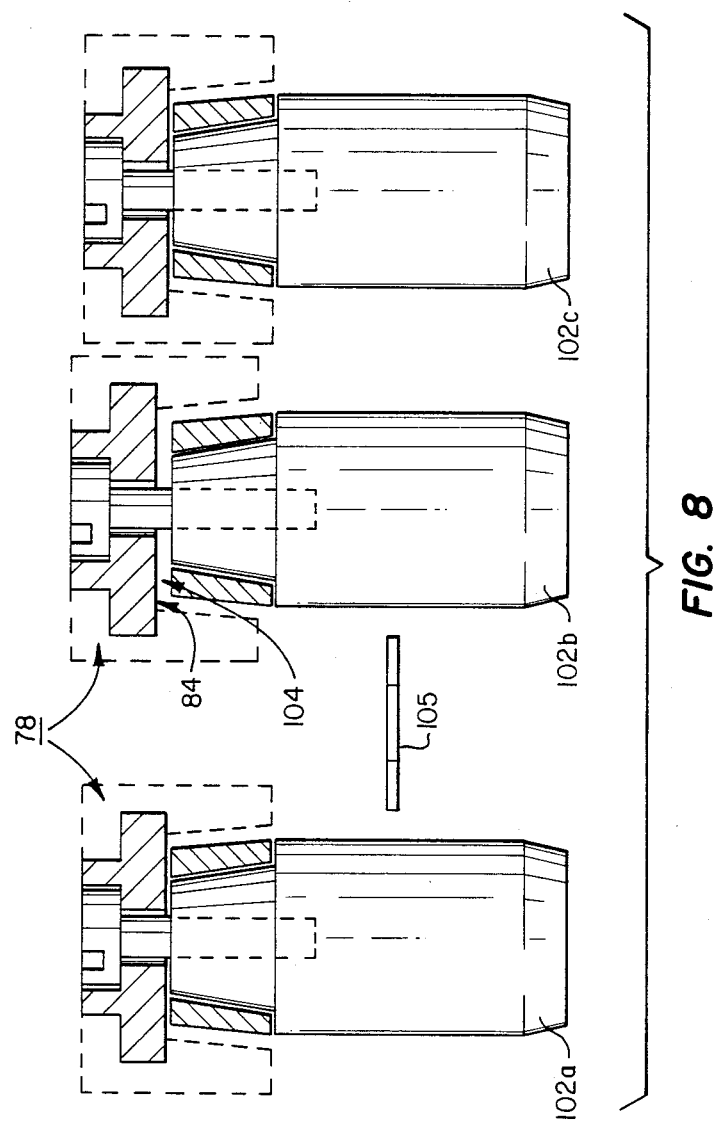

DIRECT ASSEMBLY FRAMEWORK FOR AN OSSEOINTEGRATED IMPLANT

This application is a continuation-in-part of prior copending application Ser. No. 181,919, filed Apr. 15, 1988, now U.S. Pat. No. 4,915,629.

TECHNICAL FIELD

The present invention relates generally to dental restoration and more particularly to a direct assembly framework for use in a tissue-integrated implant system.

BACKGROUND OF THE INvENTION

Many people suffer physically and psychologically from the loss of their teeth. To aid such patients, it is known in the prior art to support a denture on a bone tissue-integrated (i.e., "osseointegrated") implant. Typically, the denture is attached to a cast member which is removably secured to the implant following osseointegration and healing.

Four factors typically affect the success of the prosthesis: patient selection, fixture design and manufacture, surgical technique, and prosthetic technique. Over the last several decades, there has been considerable increase in the success rates associated with tissue-integrated implants due primarily to material advancements and improved surgical techniques. While the current success rates are impressive, there have been few improvements in the techniques used to manufacture and install the prosthesis. This fact is surprising because the prosthetic procedures are crucial to the long-term success of the tissue-integrated implant. Such procedures, however, have not changed fundamentally from techniques used to restore teeth.

To insure a successful result during installation of the prosthesis, the prosthodontist must avoid premature loading, use good bridge design, and work with great accuracy. An ideal implant-supported prosthesis would be a single unit span over all implant abutments, and would reduce the distance opposing forces between abutments could act to approximately one micrometer. Due to the properties of the materials involved, indirect laboratory techniques are not capable of constructing a large cast framework for the prosthesis to this degree of accuracy. When the resulting framework is then fitted on the implant abutments, excessive stress may be present in the system, especially at the points where the coping screws attach the cast framework to the abutments. When excessive forces are then applied to the system, the coping screws may fail or rotate from their seatings. Such imperfect adaptation may allow microscopic flexure to occur, eventual fracture of the framework, or pressure-induced resorption of the bone around the implant.

Prior attempts at reducing stress have involved sectioning the framework into one or more sections and then soldering the sections together. While soldering at one or more points may result in a stable framework, this technique has not overcome the problems of the prior art because stress will not be evenly distributed among the abutments. Moreover, soldering is an indirect procedure subject to inaccuracies, is difficult, and requires an extra appointment for the patient.

There is therefore a need for an improved framework for an osseointegrated imPlant which overcomes these and other Problems associated with prior art techniques.

BRIEF SUMMARY OF THE INVENTION

It is an object of the invention to introduce a novel framework for an osseointegrated implant which can be directly assembled intraorally.

It is yet another object of the present invention to provide a means for fixing the spatial relationship of the framework cast member and the implant abutments during direct assembly of the framework and thereby minimize stress.

It is still another object of the invention to provide a framework that is assembled intraorally and that allows a Precise adaptation of the framework to the implant-supported abutments.

In the preferred embodiment, a framework is described for a fixed/detachable prosthesis that is assembled intraorally onto at least one abutment supported by an osseointegrated implant. The framework comprises a cast member having an upper surface for supporting an aesthetic veneer and a lower surface having a recess therein, the cast member having a fastener support located above the recess and comprising a flange and a retaining wall projecting out from an upper edge of the flange. A sleeve is supported on the abutment between the abutment and the recess in the lower surface, and a preferably flathead fastener is supported in the retaining wall for securing the cast member to the abutment. A cement composition is provided in the recess in the lower surface to insure accurate adaptation of the cast member to the abutment upon installation.

The foregoing has outlined some of the more pertinent objects of the present invention. These objects should be construed to be merely illustrative of some of the more Prominent features and applications of the invention. Many other beneficial results can be attained by applying the disclosed invention in a different manner of modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference is now made to the following Description taken in conjunction with the accompanying Drawings in which:

FIG. 8 is a side view of a framework wherein a cement space is provided over an intermediate abutment through the use of a spacer.

DETAILED DESCRIPTION

Figure 1:
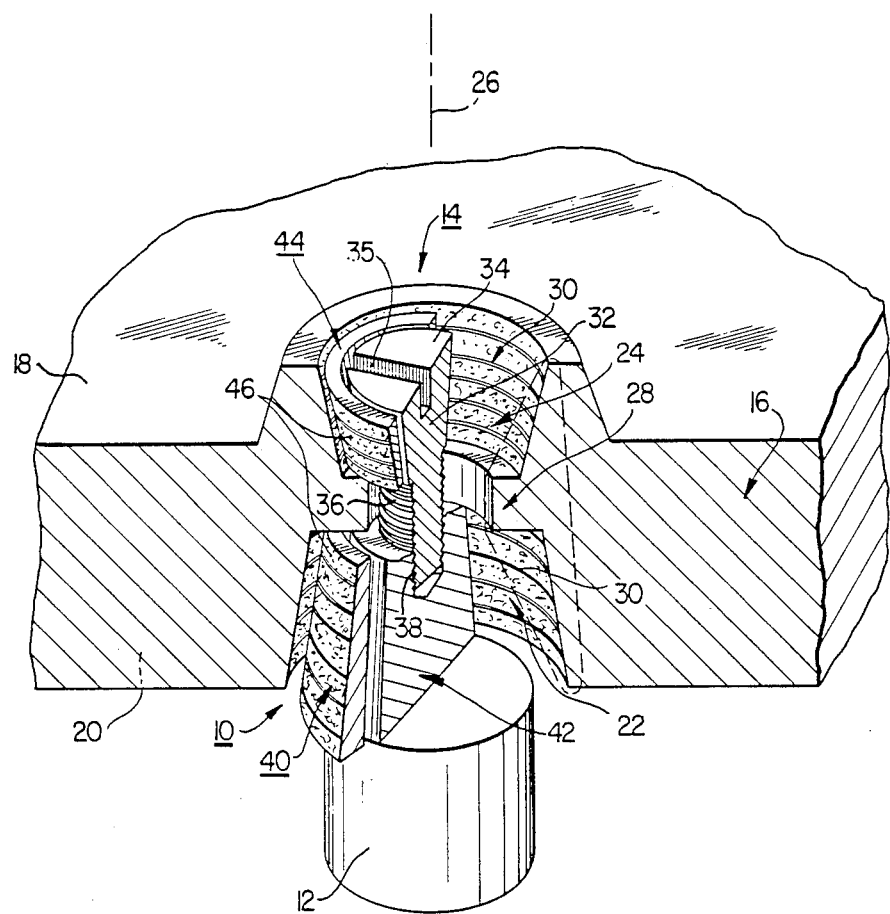
FIG. 1 is a perspective view, partially cutaway, of a portion of a framework of the present invention for use in an osseointegrated implant.

With reference now to the drawings wherein like reference numerals designate like or similar parts throughout the several views, FIG. 1 is a perspective view, partially cutaway, of a portion of a direct assembly framework 10 for use in an osseointegrated implant according to the present invention. Although not shown in detail in FIG. 1, the osseointegrated implant is surgically implanted in the jawbone of the patient and allowed to heal. Thereafter, one or more abutments, such as abutment 12, are secured to the implant in a conventional manner. Each of the abutments 12 is adapted to matingly engage an abutment support 14 of a cast member 16. The cast member 16, which has an upper surface 18 and a lower surface 20, is designed to support one or more false teeth (not shown) for the patient.

The cast member 16 is preferably a one-piece construction made from a silver-free, high content palladium alloy, a dental gold alloy, a titanium alloy, or the like. Each abutment support 14 of the cast member 16 is defined by a first taPered recess 22 in the lower surface 20 of the cast member, and a second tapered recess 24 in the upper surface 18 thereof. While the recesses are shown in FIG. 1 as being tapered, this geometry is not to be taken by way of limitation. As also seen in FIG. 1, the tapered recesses 22 and 24 are in opposed facing relation and are located along the same longitudinal axis 26. The recesses cooperate to form a ledge 28 located at approximately the midpoint of the abutment support. Each of the tapered recesses 22 and 24 also preferably has a rough surface which includes a plurality of small substantially horizontal grooves 30 therein. The grooves 30 effectively increase the surface area of the recesses for the purposes to be described. The cast member 16 is secured to the abutments of the osseointegrated implant via one or more coping screws, such as coping screw 32. Coping screw 32 comprises a substantially conical-shaped head portion 34 having a slot 35, and a threaded portion 36 adapted to engage a threaded portion 38 of the abutment 14.

Figure 2:
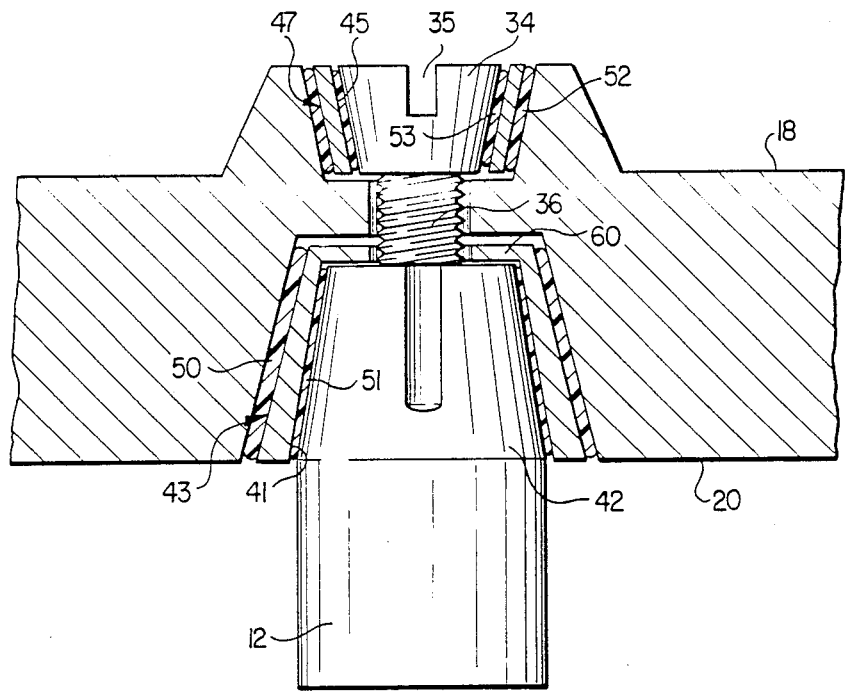
FIG. 2 is a cross-sectional view of an alternate embodiment of the framework wherein each abutment sleeve includes an integral flange.

According to a feature of the invention, the direct assembly framework 10 includes a first sleeve 40 supported on a support post 42 of the abutment 12. Although not meant to be limiting, each "abutment" sleeve 40 preferably has a substantially conical shape to matingly engage the support post 42. Of course, it should be appreciated that the shape of the sleeve 40 is a function of the shape of the abutment post. As best seen in FIG. 2, sleeve 40 includes an inner peripheral surface 41 and an outer peripheral surface 43. Likewise, the framework 10 includes a second sleeve 44 supported in the second tapered recess 24 between the head Portion 34 of the coping screw 32 and the recess. The "coping screw" sleeve 44 also has a substantially conical shape due to the shape of the screw head portion 34, although other sleeve geometries are well within the scope of the invention. Sleeve 44 includes an inner peripheral surface 45 and an outer Peripheral surface 47. The outer peripheral surfaces of the sleeves 40 and 44 are coarse and include a plurality of substantially small horizontal grooves 46 for increasing the surface area thereof. The sleeves 40 and 44 are preferably formed of dental gold, titanium or a palladium alloy.

According to a feature of the present invention, a plurality of cement layers are provided in the first and second tapered recesses 22 and 24. These layers cooperate with and are supported by the sleeves 40 and 44 to overcome the problems associated with prior art prosthetic techniques. In the preferred embodiment, each of the cement layers is formed of a self-cure crown cement composition having a polymer and an inorganic filler. One such cement composition is available from Den Mat Corporation of Santa Maria, Calif. Other types of high compression-strength cements are within the scope of the present invention. As best seen in FIG. 2, a first layer 50 of the cement composition is preferably provided between the outer peripheral surface 43 of the sleeve 40 and the first tapered recess 22. A second layer 52 is preferably located between the outer peripheral surface 47 of the sleeve 44 and the second tapered recess 24. Although not required, a third cement layer 51 may be located between the inner peripheral surface 41 of the sleeve 40 and the support post 42 of the abutment 12. Likewise, a fourth layer 53 may be located between the inner peripheral surface 45 of the sleeve 44 and the head 34 of the coping screw 32. The cement composition is designed to have a compression strength sufficiently high enough to tolerate occlusal forces and a modulus of elasticity sufficiently low enough to help absorb shocks before such forces are transmitted to the jawbone.

The cement layers are thus used to stabilize the relationship of the framework to the support points of the cast member. In this manner, the sleeves and the one or more cement layers advantageously serve to cushion forces applied to the cast member during installation and use. It should also be appreciated that the beneficial damping provided by the cement composition layers is also facilitated in part by the grooves 30 (in the recesses) and the grooves 46 (on the sleeves) which together increase the effective bonding area of the cement.

Therefore, the sleeve 40 and the cement layers 50 and 51 serve to cushion forces applied to each abutment 12. Likewise, the sleeve 44 and the cement layers 52 and 53 serve to attenuate relative movement between the coping screw 32 and the cast member 16 upon application of force to the coping screw. Together, the sleeves and the cement layers cooperate with the cast member 16 to reduce stress normally associated with a prior art osseointegrated prosthesis. Of course, although not shown in detail, it should be appreciated that each of the abutment supports of the cast member have the structure shown in FIGS. 1 and 2.

In the preferred embodiment, the crown cement composition has a compressive strength on the order of $4.1 \times 10^4$ lbs /in$^2$, a tensile strength on the order of $6.3 \times 10^3$ lbs./in$^2$ and a Young's modulus of elasticity of approximately $1.0 \times 10^6$ lbs./in$^2$. Moreover, upon final assembly of the framework, the cement layers 50–53 should be as small as possible (e.g., 0.1 millimeters) to minimize the effects of cure shrinkage (approximately 0.5%).

The various components of the direct assembly framework are custom made for the patient in accordance with the following general steps. The various abutment and coping screw sleeves may be formed from plastic telescopic copings which are normally incorporated into the waxup for the cast member. In particular, the copings are lengthened with sticky wax, cast into Type III dental gold, sectioned and then reshaped to form the sleeves 40 and 44. The sleeves are approximately 0.2 to 0.5 millimeters thick. To form the rough outer peripheral surface of each sleeve, the surface is rubbed with a coarse diamond grit. Thereafter, the small horizontal grooves are formed.

After a sufficient post-operative period, and following verification of the osseointegration with radiograph and percussion, the abutments are screwed onto the implant body. To make the first master impression of the cast member 16, a transfer coping is placed on each abutment 12 and "lifted" with the impression. The impression material used is preferably a polyether sold under the trademark IMPREGUM TM by Premier Dental Products Co. of Norristown, Penna. Aluminum transfer pins are then positioned and the impression poured with improved dental stone. A facetow transfer is then used to mount the maxillary model on a semi-adjustable articulator. Thereafter, an opposing model is mounted using a wax occlusion rim of the patient's vertical dimension in centered relation.

The sleeves 40 for the abutments are then positioned on the master model. New castable copings are fabricated from an acrylic paste to be incorporated into the waxup. Preferably, the paste is of the type marketed under the trademark DURALAY TM by Reliance Dental Mfg. Co. of Worth, Ill. A 0.1 mm thick disc of cured DURALAY TM paste is then placed over the sleeves so that a hole just large enough for a coping screw is positioned appropriately. Each coping screw 32 with its sleeve 44 in place is then positioned and screwed to the final desired position. An appropriate lubricant is then applied to the surface of the sleeves to facilitate removal of the sleeves from the castable coping. DURALAY TM paste is then added around the sleeves and the disc. After curing, the coping screws and sleeves are removed from the castable coping. Blue inlay wax is then used to add bulk to the coping as needed. The coping screws, abutment sleeves, coping screw sleeves, and castable copings are then assembled on the master cast and the cast member 16 of the direct assembly framework is then fabricated.

After the direct assembly framework 10 is fabricated, the following steps can be used to assemble the framework intraorally. When assembled, the framework will be accurate to the extent of overall cure shrinkage of the cement in the cement layers. Any abutment which does not have a common path of insertion with the other abutments must be altered in the same manner as a crown preparation until a common path of insertion exists.

The abutment sleeves are placed on their respective abutments so that marked labial or buccal sides are correct. The cast member is tried over the sleeves and relieved as needed until it is fully seated without binding against the sleeves. The coping screws and the coping screw sleeves are then placed one at a time. The cast member is relieved as needed until all of the coping screws are fully seated with the sleeves in place. Once the cast member, coping screw sleeves, abutment sleeves, and coping screws are in their proper intraoral position, these components are removed from the mouth and prepared for cementation.

A coarse diamond is first used to roughen the surface of the cast member so that the cement will contact with the small, horizontal grooves placed for tension. The cast member and sleeves are then cleaned, rinsed, dried, and arranged in sequential order for assembly. Each sleeve is specific for its location in the framework.

The dentist repositions the abutment sleeves intraorally and makes a final check of the correct sleeve position and seating. A bonding agent is applied around the sleeves and inside the first tapered recess of the cast member. Thereafter, cement paste is applied simultaneously around the abutment sleeves and inside the first tapered recesses of the cast member. This cement forms layer 50 as described above. The retentive grooves 30 and 46 should be filled and enough cement present to fill the cement space without great excess. All abutment sleeves are then cemented simultaneously to avoid possible inaccuracies and multiple seatings. The cast member is seated and held with finger pressure until the cement is completely set. The cast member is then taken from the mouth and excess cement thoroughly removed. A bonding agent is then applied to the second tapered recesses of at cast member.

Thereafter, the cast member 16 is repositioned intraorally to verify complete seating and the absolute absence of rocking motion. If rocking movement is detected, the dentist should check for cement or other debris between the cast member and the abutments. Each coping sleeve 44 is thereafter cemented singularly with its own cement mix to form layer 52. A small amount of cement paste can be mixed and then applied to a single coping screw sleeve until it is placed in a casting. Again, the grooves 30 and 46 should be filled in with enough cement to fill the cement space without great excess. After the sleeve 44 is positioned, the coping screw 32 is placed and then rotated until it is completely but very gently seated. Excess cement is then removed before the cement sets. After all the coping screw sleeves 44 are cemented, the coping screws 32 are removed and cleaned of excess cement. The heads 34 of the coping screws may be shortened and the height of the cast member reduced as needed. The framework assembly is now complete. The framework should fit the prosthetic abutments with an accuracy on the order of $10^{-4}$ mm. A well-made one-piece cast member will have a marginal gap of approximately 10 micrometers.

Referring back now to FIG. 2, a cross-sectional view is shown of an alternate embodiment of the direct assembly framework of FIG. 1. In the alternate embodiment of FIG. 2, each of the abutment sleeves 40 includes an integral flange 60 located at an upper end thereof to facilitate the proper seating of the cast member 16 on the associated abutment.

Figure 3:
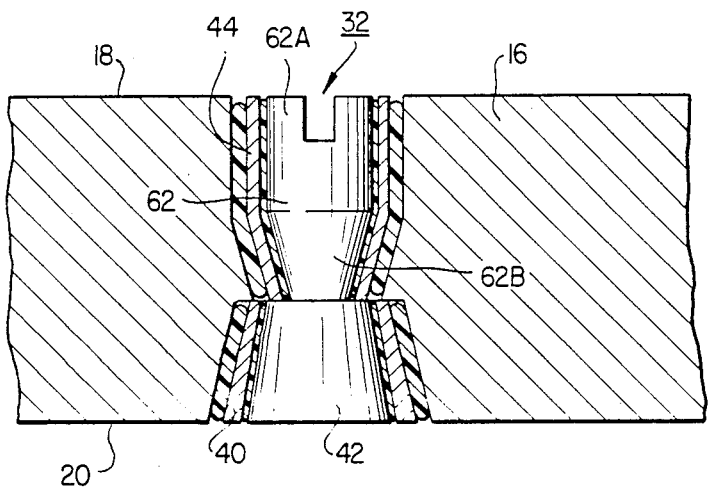
FIG. 3 is a cross-sectional view of another embodiment of the framework for use with a modified type of coping screw.

As noted above, the geometry of each of the coping screw sleeves is also a direct function of the geometry of the coping screw itself. In particular, and with reference to FIG. 3, a cross-sectional view is shown of yet another embodiment of the direct assembly framework. wherein the coping screw 32 includes a head 62 having an upper portion 62A and a lower portion 62B substantially as shown in FIG. 3. When this tYpe of geometry is used for the coping screw, the coping screw sleeve 44 is required to have substantially the shape shown in FIG. 3.

In summary, according to the invention a direct assembly framework is provided comprising a cast member, one or more abutment sleeves, one or more coping sleeves, one or more coping screws and one or more cement layers for securing these components against relative movement The sleeves are preferably made of dental gold or titanium, and the cement is a self-cured composite resin. The direct assembly of the framework is accomplished intraorally. The prosthesis is constructed and installed in a way which is much more accurate than is possible with prior art indirect laboratory techniques. Soldering and other prior art approaches required to compensate for inaccuracies and defects are therefore not needed. The resulting bone-fixture-prosthesis system is free of internal stress for any number of implants in any length of prosthesis. Moreover, the direct assembly framework advantageously reduces the distance opposing forces act on abutments to a range of 0.5 to 2.5 micrometers.

Figure 4:
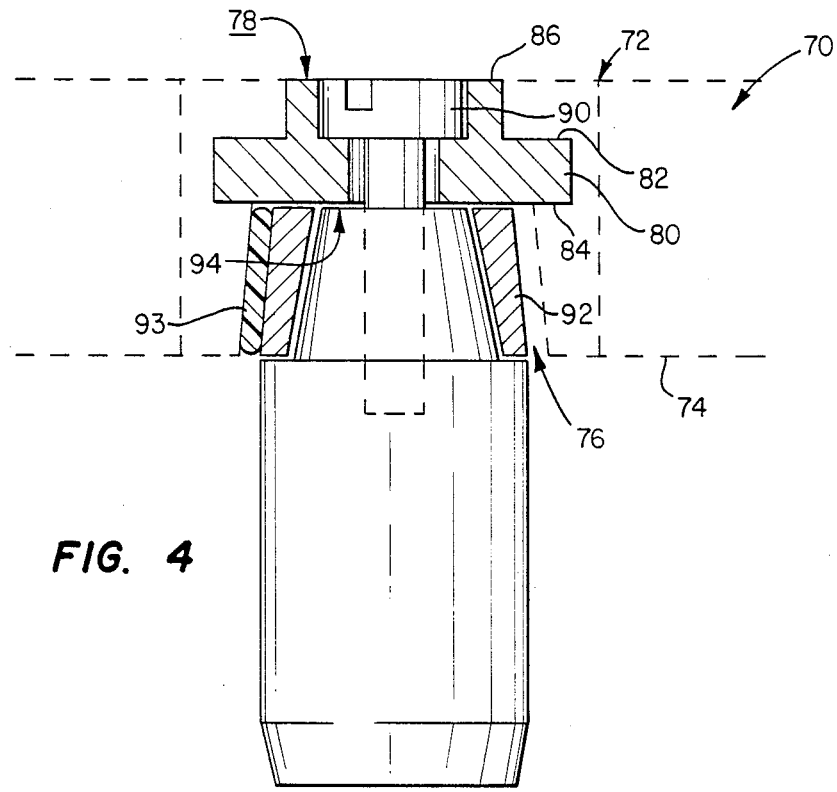
FIG. 4 is a side view of an alternate embodiment of the invention wherein the cast member includes a fastener support for use with a flathead type retaining screw.
Figure 5:
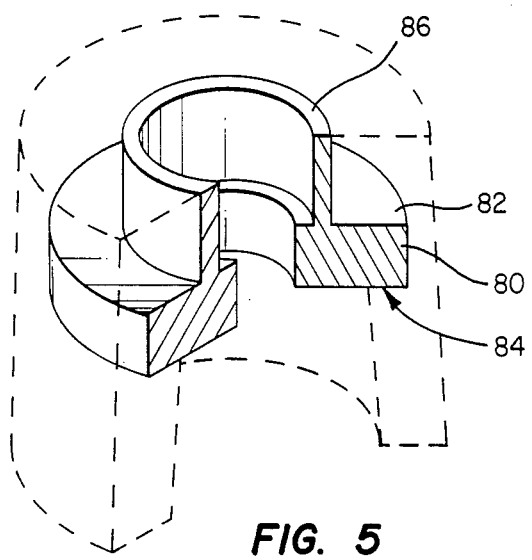
FIG. 5 is a perspective view of the fastener support of FIG. 4.

According to an alternate embodiment of the present invention, it is desirable to use a cast member having one or more preformed fastener supports to functionally replace the ledge 28 of the cast member and the second sleeve 44 as described above with respect to FIG. 2. Referring now to FIGS. 4-5, in this embodiment the cast member 70 has an upper surface 72 for supporting an aesthetic veneer (not shown) and a lower surface 74 having a recess 76 therein. The fastener support is designated generally by the reference numeral 78 and is located generally above the recess 76. Fastener support 78 is preferably preformed of stainless steel or a gold alloy and comprises a flange 80 having an upper edge 82 and a lower edge 84. A retaining wall 86 projects transversely from the upper edge 82 of the flange 80 for supporting a fastener 90 such as a flathead coping screw. The screw serves to secure the cast member to the abutment. As described above, preferably the framework also includes a sleeve 92 supported on the abutment between the abutment and the recess in the lower surface. Suitable cement composition means 93 is located in the recess in the lower surface to provide accurate adaptation of the cast member to the abutment upon installation of the cast member.

The preformed internal flange 80 is advantageous because it provides smooth machined surfaces for contact with an upper end 94 of the abutment, an upper end of the sleeve and the bottom surface of the head of the coping screw 90. This structure provides ease of installation over the ledge 28, which is often difficult to form without uneven surfaces. The preformed fastener support 78 is preferably incorporated into the wax framework before casting the cast member. The retaining wall 86 thus serves to advantageously prevent metal (of the remainder of the cast member) from entering the coping screw receptor site during casting.

Moreover, the preformed fastener support 78 advantageously enables the use of the flathead coping screw 90 instead of a conical screw as described above with respect to FIG. 2. Use of the retaining screw sleeve, i.e., second sleeve 44, is thus obviated because turning forces are directed vertically with a flathead screw rather than laterally as with a conical screw. Therefore, in the embodiment shown in FIGS. 4-5, only the abutment sleeve is required.

Figure 6:
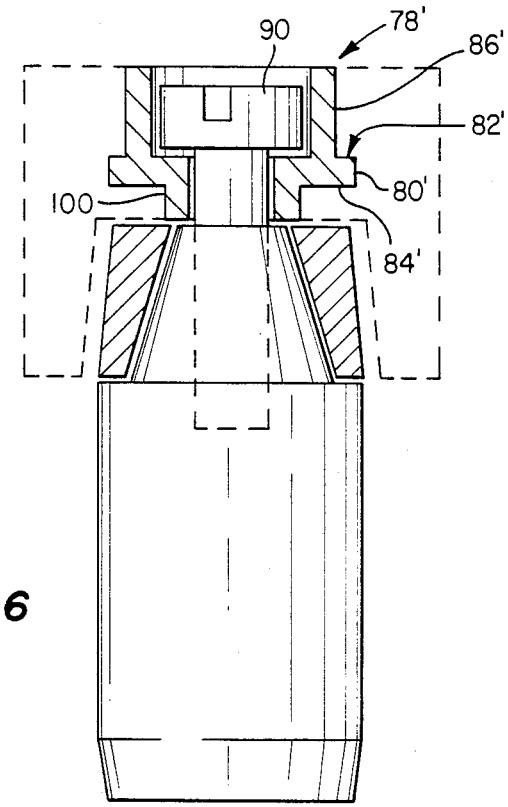
FIGS. 6–7 show an alternate embodiment of the fastener support of FIGS. 4–5.
Figure 7:
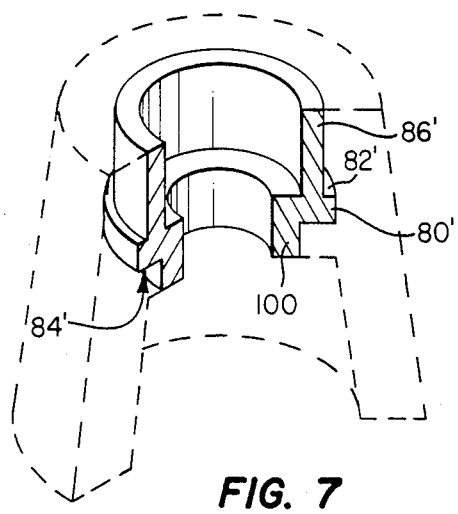

Referring now to FIGS. 6-7, an alternate embodiment of the fastener support 78' is provided. In this embodiment, the fastener support 78' comprises a flange 80 having an upper edge 82' and a lower edge 84. A retaining wall 86' projects transversely from the upper edge 82' of the flange 80' for supporting a fastener 90 such as a flathead coping screw. The fastener support also includes a second retaining wall 100 projecting out from the lower edge 84' of the flange. The structure of FIGS. 7-8 is advantageous because it reduces the size of the internal flange but stil provides adequate support for the screw.

FIG. 8 shows a side view of a plurality of abutments 102a, 102b and 102c each cooperating with a fastener support 78 as described above with respect to FIG. 5. Primary support in a full arch prosthesis usually involves the most distal abutment on each side and the most anterior abutment. Preferably, a tripod support is established Abutments between the primary abutments, such as abutment 102b, may include a cement space 104 between the lower edge 84 and the top of the abutment. This space is created by using a removable spacer 105 between the flange and the abutment when the framework is waxed and then removing the spacer before casting. The space is then filled with the cement composition and advantageously prevents interference with complete seatinq of the framework.

Although the invention has been described and illustrated in detail, it should appreciated that the same is by way of illustration only, and is not to be taken by way of limitation. The spirit and scope of the present invention are limited only to the terms of the appended claims.

I claim:

1. A framework for a fixed/detachable prosthesis that is assembled intraorally onto at least one abutment supported by an osseointegrated implant, the framework comprising:
   a cast member having an upper surface for supporting an aesthetic veneer and a lower surface having a recess therein, the cast member having fastener support means located above the recess and comprising a flange and a retaining wall projecting out from an upper edge of the flange;
   a sleeve supported on the abutment between the abutment and the recess in the lower surface;
   a fastener supported in the retaining wall for securing the cast member to the abutment; and
   cement means located in the recess in the lower surface to provide accurate adaptation of the cast member to the abutment upon installation of the cast member.

2. The framework as described in claim 1 wherein the fastener support means includes a retaining wall projecting out from a lower edge of the flange.

3. The framework as described in claim 1 wherein the cement means is a cement composition having a compression strength sufficiently high enough to tolerate occlusal forces on the osseointegrated implant and having a modulus of elasticity sufficiently low enough to absorb shocks.

4. The framework as described in claim 3 wherein the cement means includes a layer located between an outer peripheral surface of the sleeve and the recess.

5. The framework as described in claim 4 wherein the outer peripheral surface of the sleeve is coarse and includes a plurality of grooves for increasing the area of said outer peripheral surface.

6. The framework as described in claim 5 wherein the grooves are substantially horizontal.

7. The framework as described in claim 4 wherein the tapered recess is coarse and includes a plurality of grooves for increasing the surface area thereof.

8. The framework as described in claim 7 wherein each of the grooves is substantially horizontal.

9. A framework for a fixed detachable prosthesis that is assembled intraorally onto abutments supported by osseointegrated implants, the framework comprising:
   a cast member having an upper surface for supporting an aesthetic veneer and a lower surface each including a plurality of recesses therein, the cast member having a plurality of fastener support means each located above one of the recesses and comprising a flange and a retaining wall projecting out from an upper edge of the flange;
   a sleeve supported on each abutment;

a fastener supported in the retaining wall of at least one of the fastener support means for securing the cast member to the abutments; and cement means located in the recesses in the lower surface to provide accurate adaptation of the cast member to the abutments upon installation of the cast member.

10. The framework as described in claim 9 wherein at least one of the fastener support means is spaced from a top edge of the abutment upon installation of the cast member.

11. The framework as described in claim 10 wherein the cement means is located in a space between the top edge of the abutment and a lower edge of the flange.

* * * * *